(12) United States Patent
Inaba et al.

(10) Patent No.: US 6,262,315 B1
(45) Date of Patent: Jul. 17, 2001

(54) PROCESS AND APPARATUS FOR PRODUCING DIHYDRIC PHENOLIC COMPOUND

(75) Inventors: Yukio Inaba; Kazunori Fujita; Hiroshi Kofuji, all of Ube (JP)

(73) Assignee: Ube Industries, Ltd., Yamaguchi (JP)

( * ) Notice: Subject to any disclaimer, the term of this patent is extended or adjusted under 35 U.S.C. 154(b) by 0 days.

(21) Appl. No.: 09/320,094

(22) Filed: May 26, 1999

(30) Foreign Application Priority Data

May 29, 1998 (JP) .................................................. 10-149471

(51) Int. Cl.[7] .................................................. C07C 37/00
(52) U.S. Cl. ............................................ 568/771; 422/189
(58) Field of Search ............................................... 568/771

(56) References Cited

U.S. PATENT DOCUMENTS

| 3,849,502 | 11/1974 | Bourdin et al. . |
| 4,072,722 | 2/1978 | Umemura et al. . |
| 4,078,006 | 3/1978 | Umemura et al. . |
| 5,493,061 | 2/1996 | Ratnasamy et al. . |

FOREIGN PATENT DOCUMENTS

| 2 064 497 | 12/1970 | (DE) . |
| 50-142518 | 11/1975 | (JP) . |
| 50-142519 | 11/1975 | (JP) . |

OTHER PUBLICATIONS

European Search Report (1999).

*Primary Examiner*—Michael L. Shippen
(74) *Attorney, Agent, or Firm*—Burgess, Ryan & Wayne; Milton J. Wayne; William R-Moran

(57) ABSTRACT

A dihydric phenolic compound is produced, with a high selectivity thereof, by a plurality of oxidation reactors connected to each other in series, by (1) feeding a monohydric phenolic compound with a temperature of 30 to 100° C., a peroxide compound, a catalyst and optionally a ketone compound into a first reactor to oxidize the monohydric phenolic compound, and delivering a resultant reaction mixture containing the produced dihydric phenolic compound and non-reacted monohydric phenolic compound from the first reactor; (2) passing the reaction mixture through one or more reactors succeeding to the first reactor, to further oxidize the monohydric phenolic compound, while, in the steps (1) and (2), a portion of the peroxide compound is fed into the first reactor and the remaining portion of the peroxide compound is fed into at least one succeeding reactor; and (3) delivering a first reaction mixture produced in a rearend reactor and comprising the produced dihydric phenolic compound, the non-reacted monohydric phenolic compound and peroxide compound and the catalyst from the rearend reactor.

13 Claims, 2 Drawing Sheets

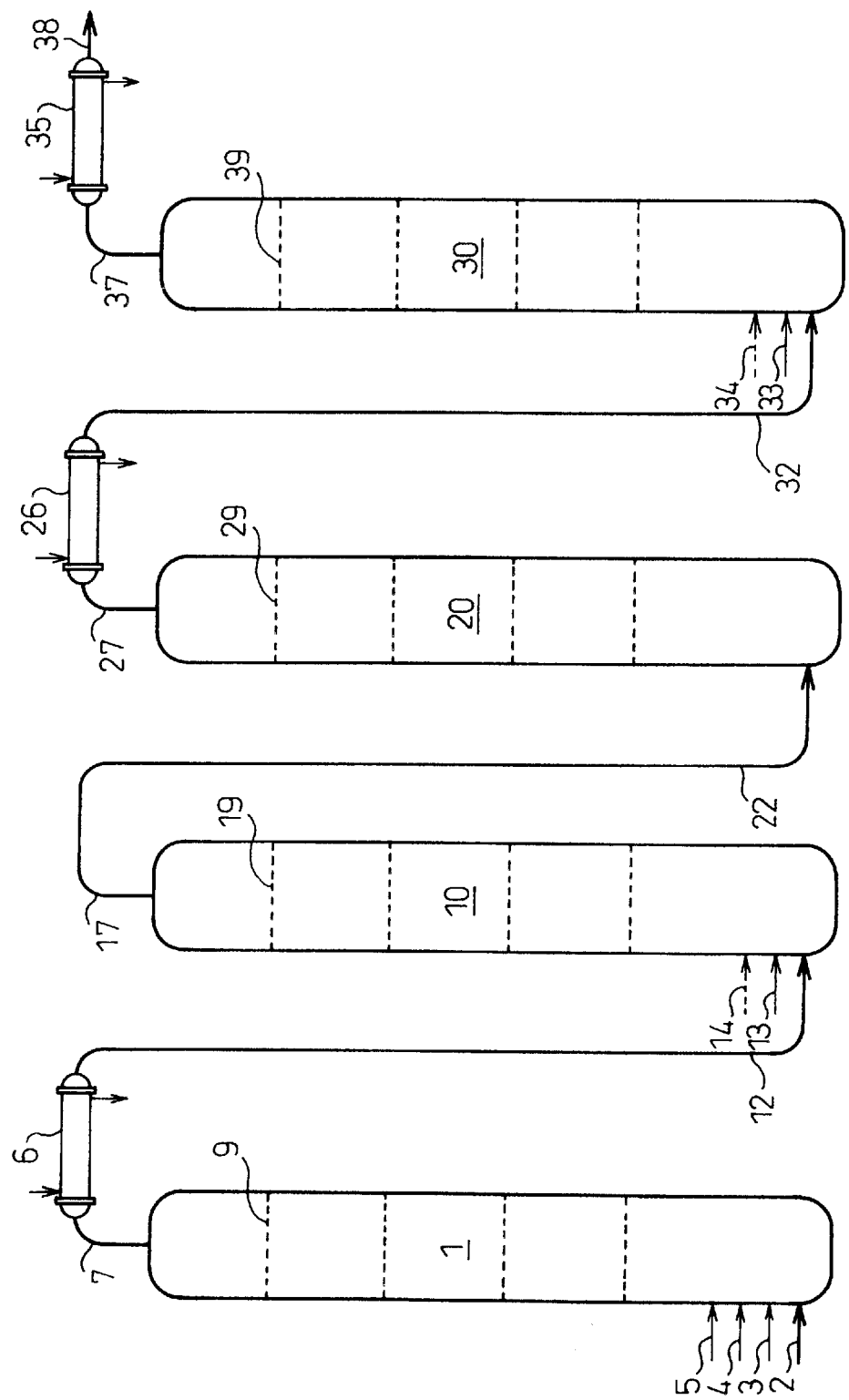

PROCESS AND APPARATUS FOR PRODUCING DIHYDRIC PHENOLIC COMPOUND

BACKGROUND OF THE INVENTION

1. Field of the Invention

The present invention relates to a process and apparatus for producing a dihydric phenolic compound. More particularly, the present invention relates to a process and apparatus for producing a dihydric phenolic compound at a high stability and safety, at a high selectivity and with a high efficiency.

Still more particularly, the present invention relates to a process and apparatus for producing a dihydric phenolic compound, for example, catechol or hydroquinone, from a monohydric phenolic compound at an excellent selectivity at a high stability, while containing the reaction liquid temperature of the monohydric phenolic compound in an appropriate range, which process and apparatus are suitable for industrial practice.

2. Description of the Related Art

Processes for producing a dihydric phenolic compound, for example, catechol together with hydroquinone by an oxidation reaction of monohydric phenolic compounds with peroxide compounds, for example, hydrogen peroxide and ketone peroxide, in the presence of specific catalysts are well known from, for example, Japanese Examined Patent Publications No. 52-38,546 (corresponding to U.S. Pat. No. 4,078,006), No. 52-38,547 (corresponding to U.S. Pat. No. 4,072,722), No. 52-38,548 and No. 52-38,549.

In the conventional processes for producing dihydric phenolic compounds, however, an industrial means for industrially and easily controlling the rapid temperature rise in the reaction liquid for the oxidation reaction of the monohydric phenolic compound due to the heat generated by reaction has not been concretely known. Therefore, the conventional processes are disadvantageous in that not only an explosion of ketoneperoxide contained in the reaction liquid cannot be surely prevented, but also the selectivity of the target dihydric phenolic compound significantly decreases due to the rapid rise of the reaction liquid temperature, and the yield of the dihydric phenolic compound decreases. Accordingly, when a high safety of the reaction procedure and a high selectivity of the target dihydric phenolic compound are required above all, the reaction procedure must be carried out at a low conversion of the monohydric phenolic compound.

SUMMARY OF THE INVENTION

An object of the present invention is to provide a process and apparatus for providing dihydric phenolic compounds by a continuous oxidation reaction of a monohydric phenolic compound, at enhanced selectivity and yield of the target dihydric phenolic compound, while preventing a rapid rise of the reaction liquid temperature due to a generation of heat of reaction and maintaining a conversion of the monohydric phenolic compound at a satisfactory level, which process and apparatus are suitable for industrial continuous production of the dihydric phenolic compounds.

The above-mentioned object can be attained by the process and apparatus of the present invention.

The process of the present invention for producing dihydric phenolic compound comprises oxidizing a monohydric phenolic compound in the presence of a catalyst by using a continuous multi-stage oxidation apparatus comprising a plurality of oxidation reactors connected to each other in series in such a manner that (1) in a first reactor of the oxidation apparatus, a monohydric phenolic compound having a temperature of 30 to 100° C., a peroxide compound and a catalyst are fed thereinto, to oxidize the monohydric phenolic compound into a dihydric phenolic compound, and the resultant reaction mixture containing the produced dihydric phenolic compounds, the non-reacted monohydric compound, the non-reacted peroxide compound and the catalyst is delivered from the first reactor; (2) the reaction mixture delivered from the first reactor is passed through one or more reactors succeeding to the first reactor, to further oxidize the non-reacted monohydric phenolic compound, while, in the steps (1) and (2), a portion of the peroxide compound is fed into the first reactor and the remaining portion of the peroxide compound is fed into at least one succeeding reactor; and (3) a final reaction mixture produced in a rearend reactor and comprising the produced dihydric phenolic compound, the non-reacted monohydric phenolic compound, the non-reacted peroxide compound and the catalyst is delivered from the oxidation apparatus.

In the dihydric phenolic compound-producing process of the present invention, optionally, at least one ketone compound is fed together with the monohydric phenolic compound, the peroxide compound and the catalyst into the first reactor.

In the dihydric phenolic compound-producing process of the present invention optionally, before the remaining portion of the peroxide compound is fed into at least one reactor succeeding to the first reactor, the reaction mixture delivered from a next reactor located in front of the succeeding reactor to which the remaining portion of the peroxide compound is fed is cooled to a temperature of 40 to 100° C. by a cooling means, and then is fed, together with the remaining portion of the peroxide compound, into the succeeding reactor, and the temperature of the reaction mixture passing through the oxidation apparatus is controlled to a level of 40 to 120° C.

The continuous multi-stage oxidation apparatus of the present invention for producing dihydric phenolic compounds by the process of the present invention as defined above, comprises a first reactor and one or more reactors succeeding the first reactor which reactors are connected to each other in series, and are each suitable for catalytically oxidizing a monohydric phenolic compound into dihydric phenolic compounds, wherein the first reactor is connected to a feed source of a monohydric phenolic compound, a feed source of a peroxide compound and a feed source of a catalyst, at least one succeeding reactor is connected to a feed source of the peroxide compound, and a rearend reactor has an outlet for delivering a final reaction mixture produced therein.

In the dihydric phenolic compound-producing apparatus of the present invention, optionally, the first reactor is further connected to a feed source of a ketone compound.

The dihydric phenolic compound-producing apparatus of the present invention optionally further comprises a cooling means arranged between the succeeding reactor connected to the peroxide compound-feed source and a next reactor located in front of the succeeding reactor connected to the peroxide compound-feed source.

BRIEF DESCRIPTION OF THE DRAWINGS

FIG. 2 is an explanatory flow sheet showing another embodiment of the process of the present invention using a continuous four stage oxidation apparatus.

DESCRIPTION OF THE PREFERRED EMBODIMENTS

Figure 1:
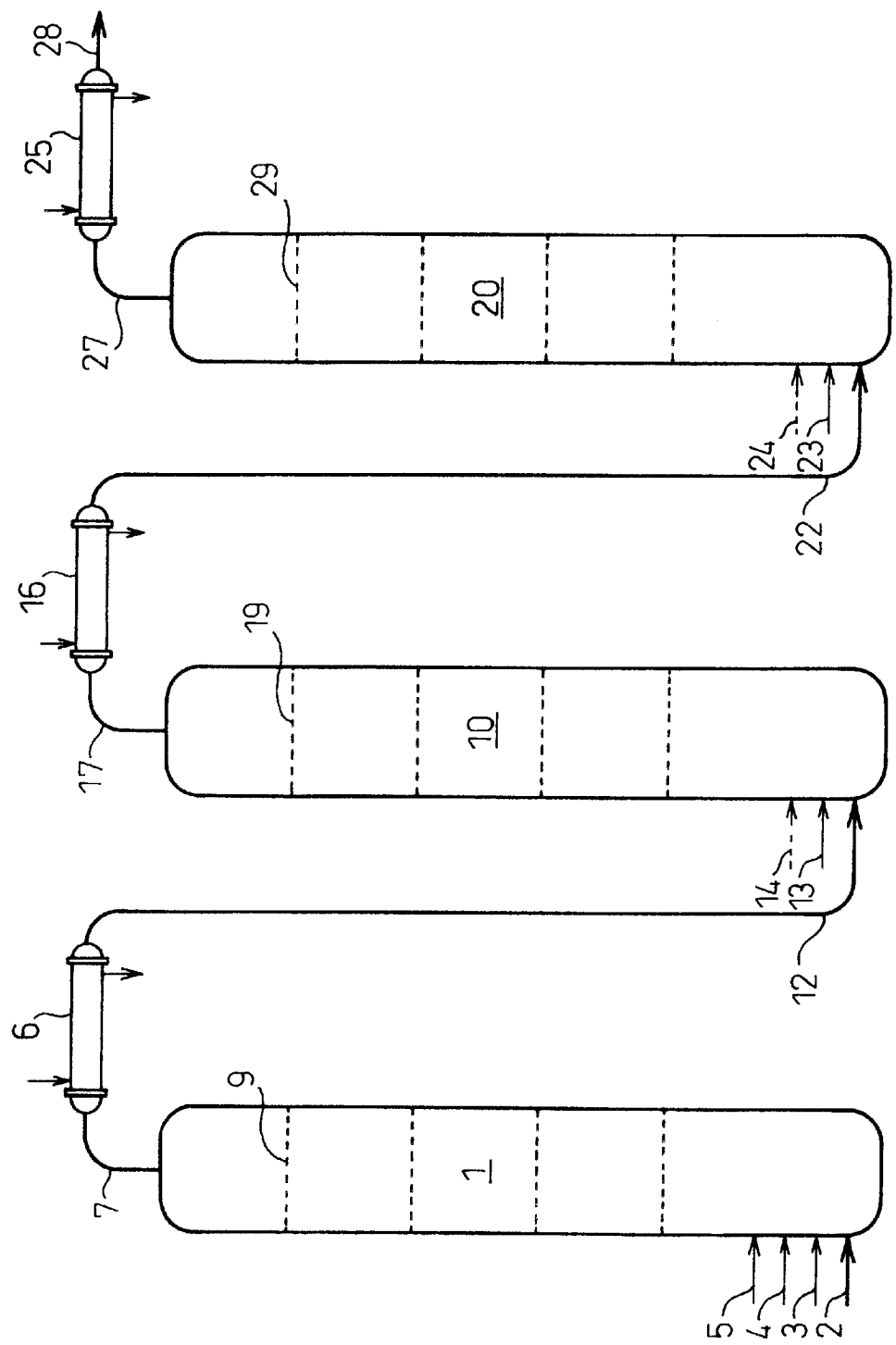
FIG. 1 is an explanatory flow sheet showing an embodiment of the process of the present invention using a continuous three stage oxidation apparatus.

In the process of the present invention for producing dihydric phenolic compounds by oxidizing a monohydric phenolic compound in the presence of a catalyst, a continuous multi-stage oxidation apparatus comprising a plurality of oxidation reactors connected to each other in series is used.

The continuous multi-stage oxidation apparatus preferably comprises 2 to 10 reactors, more preferably 2 to 6 reactors, still more preferably 3 to 5 reactors, connected to each other in series.

In the process of the present invention, (1) in a first reactor of the oxidation apparatus, a monohydric phenolic compound having a temperature of 30 to 100° C., a peroxide compound and a catalyst are fed thereinto, to oxidize the monohydric phenolic compound into dihydric phenolic compounds, and the resultant reaction mixture containing the produced dihydric phenolic compounds, the non-reacted monohydric compound, the non-reacted peroxide compound and the catalyst is delivered from the first reactor;

(2) the reaction mixture delivered from the first reactor is passed through one or more reactors succeeding to the first reactor, to further oxidize the non-reacted monohydric phenolic compound, while in the steps (1) and (2), a portion of the peroxide compound being fed into the first reactor and the remaining portion of the peroxide compound being fed into at least one succeeding reactor;

(3) a final reaction mixture produced in a rearend reactor and comprising the produced dihydric phenolic compounds, the non-reacted monohydric phenolic compound, the non-reacted peroxide compound and the catalyst is delivered from the oxidation apparatus.

The process and apparatus of the present invention will be explained in detail below, while referring to the attached drawings.

Referring to FIG. 1, three oxidation reactors 1, 10 and 20 are successively connected to each other in series. Into a lower portion of the first reactor 1, a monohydric phenolic compound, for example, phenol, having a temperature of 30 to 100° C., preferably 40 to 95° C. is fed from a supply source thereof (not shown) through a feed line 2, a peroxide compound, for example, a portion of hydrogen peroxide, is fed from a supply source thereof (not shown) through a feed line 3, a catalyst is fed from a supply source thereof (not shown) through a feed line 4, and optionally, a ketone compound is fed from a supply source thereof (not shown) through a feed line 5. In the first reactor 1, the monohydric phenolic compound is catalytically oxidized with the peroxide compound to produce dihydric phenolic compounds as target products. The feed lines 2, 3, 4 and 5 are connected, at locations close to each other, to the lower portion of the first reactor 1. The resultant reaction mixture produced in the first reactor 1 and containing the produced dihydric phenolic compounds, the non-reacted monohydric phenolic compound, the non-reacted peroxide compound, the catalyst and optionally the non-reacted ketone compound is delivered from the top portion of the first reactor 1 through a delivery line 7, is cooled by a cooler 6, for example, a heat-exchanger type cooler, to a temperature of 40 to 100° C., and then the cooled reaction mixture is fed into a lower portion of a second reactor 10 through a feed line 12. Into the lower portion of the second reactor 10, another portion of the peroxide compound is fed from a supply source thereof (not shown) through a feed line 13 and optionally an additional amount of the catalyst is fed from a supply source thereof (not shown) through a feed line 14, to further oxidize the monohydric phenolic compound into the dihydric phenolic compounds.

The feed lines 12, 13 and 14 are connected at locations close to each other, to the lower portion of the second reactor 10.

The resultant reaction mixture produced in the second reactor 10 and containing the produced dihydric phenolic compound the non-reacted monohydric phenolic compound, the non-reacted peroxide compound, the catalyst and optionally the non-reacted ketone compound is delivered from the top portion of the second reactor 10 through a delivery line 17, is cooled by a cooler 16 to a temperature of 40 to 100° C., and then the cooled reaction mixture is fed into a lower portion of a third reactor 20 through a feed line 22. Into the lower portion of the third reactor 20, the remaining portion of the peroxide compound is fed from a supply source thereof (not shown) through a feed line 23 and optionally a further additional amount of the catalyst is fed from a supply source thereof (not shown) through a feed line 24, to further oxidize the monohydric phenolic compound into the dihydric phenolic compounds.

The feed lines 22, 23 and 24 are connected at locations close to each other, to the lower portion of the third reactor 20.

The reaction mixture produced in the third reactor 20 and containing the target dihydric phenolic compound, the catalyst and the non-reacted monohydric phenolic compound, peroxide compound and optionally ketone compound (which may not be contained) is delivered from the top portion of the third reactor 20 through a delivery line 27. The delivered reaction mixture is cooled or heated to a desired temperature by a heat-exchanger 25 and then withdrawn from the continuous oxidation apparatus through a withdrawal line 28.

When the peroxide compound is fed into at least one of the reactors succeeding to the first reactor, the reaction mixture delivered from a next reactor located in front of the succeeding reactor into which the peroxide compound is supplemented is preferably cooled by a cooler to a temperature of 40 to 100° C., more preferably 50 to 100° C. and then fed into the succeeding reactor. By feeding the peroxide compound into two or more reactors, the monohydric phenolic compound can be converted to dihydric phenolic compounds with a high selectivity of the dihydric phenolic compounds.

In each of the oxidation reactors, the reaction mixture flows upward and the temperature of the reaction mixture is preferably controlled to 40 to 120° C., more preferably 55 to 115° C.

In the process and apparatus of the present invention, the oxidation reaction apparatus preferably includes 2 to 10 reactors, more preferably 2 to 6 reactors, still more preferably 3 to 4 reactors, connected to each other in series.

In this oxidation reaction apparatus, the peroxide compound, for example, hydrogen peroxide is dividedly fed into the first reactor and to at least one of the succeeding reactors, preferably 1 to 8, more preferably 1 to 5, still more preferably 2 to 3 of the succeeding reactors.

In the process of the present invention, the catalyst may be fed in a whole amount into the first reactor. Alternatively a portion of the catalyst may be fed into the first reactor and the remaining portion of the catalyst may be fed into one or more of the succeeding reactors. Preferably, the catalyst is dividedly fed into the first reactor and to at least one of the succeeding reactors into which a portion of the peroxide compound is fed. For example, in the multi-stage oxidation apparatus as shown in FIG. 1, a portion of the total amount of the peroxide compound is fed into the first reactor 1 through the feed line 3, and the remaining portion of the peroxide compound is fed dividually into the second and third reactors through the feed lines 13 and 23, respectively.

Also, a portion of the total amount of the catalyst is fed into the first reactor 1 through the feed line 4, and the remaining portion of the catalyst is fed dividedly fed into the second and third reactors 10 and 20 through the feed lines 14 and 24, respectively.

In the process of the present invention, the production reaction for the dihydric phenolic compounds, namely the oxidation reaction of the monohydric phenolic compound, in the oxidation reaction apparatus is preferably carried out to such an extent that the monohydric phenolic compound is reacted at a low conversion of 0.1 to 10 molar %, more preferably 0.3 to 6 molar %, and the peroxide compound, particularly hydrogen peroxide, is reacted at a high conversion of 80 to 100 molar %, more preferably 95 to 100 molar %. For this purpose, the total amount of the monohydric phenolic compound and the total amount of the peroxide compound fed into the multi-stage oxidation apparatus are preferably in a molar ratio of 10:1 to 100:1, more preferably 17:1 to 33:1. This specific range of the molar ratio of the monohydric phenolic compound to the peroxide compound contributes to obtaining the dihydric phenolic compounds at a high selectivity thereof.

In the process of the present invention, the production of the dihydric phenolic compound in each reactor of the multi-stage oxidation apparatus is preferably carried out to such an extent that the monohydric phenolic compound is reacted at a very low conversion of 0.1 to 3 molar %, more preferably 0.5 to 2 molar %, and the peroxide compound is reacted at a high conversion of 70 to 100 molar %, more preferably 75 to 100%. The very low conversion of the monohydric phenolic compound and the high conversion of the peroxide compound contribute to preventing or restricting an irregular rapid rise in the temperature of the reaction mixture.

In this case, the amount of the monohydric phenolic compound fed into the first reactor and the amount of the peroxide compound fed into each of the reactors to which the peroxide compound are preferably in a molar ratio of 33:1 to 1000:1, more preferably 50:1 to 200:1, to decrease the conversion of the monohydric phenolic compound in each of the reactors and to restrict the exothermic reaction of the monohydric phenolic compound.

In the process of the present invention, the temperature of the reaction mixture delivered from a flow end portion of the each reaction, namely, when the material or the reaction mixture is fed into a bottom portion of the reactor, a top portion of the reactor is the flow end portion of the reactor and is preferably maintained at a level of 120° C. or less, more preferably 115° C. or less, to prevent side reactions and to increase the selectivity of the dihydric phenolic compound.

Also, in the process of the present invention, the increase in temperature of the reaction mixture between the feed inlet portion and the delivery outlet portion of each reactor is preferably controlled to 3 to 30° C., more preferably 5 to 20° C., to maintain the conversion of the monohydric phenolic compound due to the oxidation reaction thereof at a low level.

The monohydric phenolic compound usable for the process of the present invention includes phenolic compounds having a hydroxyl group attached to a benzene ring, for example, phenol, o-, m- and p-cresols, o-, m- and p-ethylphenols, o-, m- and p-(n-propyl)phenols, o-, m- and p-isopropylphenols, o-, m- and p-(n-butyl)phenols, o-, m- and p-isobutyl phenols, o-, m- and p-(tert-butyl)phenols, p-pentylphenol, p-hexylphenol 2,3,6-trimethylphenol and methylsalicylate. The phenol is preferred for the process of the present invention.

The dihydric phenolic compounds which can be produced by the process of the present invention are, phenolic compounds having two hydroxyl groups attached to a benzene ring, for example catechol, hydroquinone, 3-methyl-catechol, 2-methylhydroquinone, 4-methyl catechol, 3-ethylcatechol, 2-ethylhydroquinone, 4-ethylcatechol, 3-propylcatechols, 2-propylhydroquinones, 4-propylcatechols, n-butylcatechols, 2-butylhydroquinones, 4-butyl-catechols, 4-pentylcatechol, 4-hexylcatechol, 2,3,5-trimethylhydroquinone and methyl 2,5-dihydroxybenzoate.

The phenol can be converted to catechol and hydroquinone, the o-cresol to 3-methylcatechol and 2-methyl-hydroquinone, the m-cresol to 3-methyl catechol, 2-methylhydroquinone and 4-methylcatechol and p-cresol to 4-methylcatechol.

The peroxide compound usable for the process of the present invention, is selected from inorganic peroxide compounds, for example, hydrogen peroxide and perchloric acid and organic peroxide compounds, for example, ketone peroxides and aliphatic percarboxylic acids. In the process of the present invention, hydrogen peroxide, ketone peroxides and mixtures of hydrogen peroxide and a ketone compound are preferably employed. When the peroxide compound is dividedly fed into a plurality of reactors of the multi-stage oxidation apparatus of the present invention, hydrogen peroxide is more preferably employed as a peroxide compound.

The ketone compound which is optionally employed in the process of the present invention, is preferably selected from aliphatic dialkyl ketones which more preferably have 3 to 20 carbon atoms, for example, dimethylketone, diethylketone, diisopropylketone, diisobutylketone, methylethylketone, methyl-n-propylketone, methylisopropylketone, methylisobutylketone, ethylisopropylketone, ethylisobutylketone and ethylhexylketone. In the process of the present invention, more preferably, the ketone compound is selected from aliphatic di-lower alkyl ketones of which each alkyl group has 1 to 9 carbon atoms, for example, dimethylketone, diethylketone, di-n-propylketone and diisopropylketone.

In the process of the present invention, optionally, the ketone compound is preferably employed in a total amount of 0.5 to 10% by weight, more preferably 1 to 5% by weight, based on the amount of the monohydric phenolic compound fed into the first reactor, and in a total molar amount of 0.1 to 10 moles, more preferably 1 to 5 moles, per mole of the peroxide compound fed into the multi-stage oxidation apparatus.

The ketone peroxides usable as a peroxide compound for the process of the present invention, are preferably selected from dialkylketone peroxides, for example, dimethylketone peroxide, diethylketone peroxide, diisopropylketone peroxide, diisobutyl peroxide, methylethylketone peroxide, methyl-n-propylketone peroxide, methyl-isopropylketone peroxide, methylisobutylketone peroxide, ethyl-isopropylketone peroxide, and ethylisobutylketone peroxide.

The aliphatic percarboxylic acids usable for the process of the present invention are selected from, for example, peracetic acid and perpropionic acid.

The oxidation catalyst usable for the process of the present invention may be selected from conventional catalysts usable for oxidation reactions. Preferably, the catalyst comprises at least one member selected from phosphoric acid, sulfuric acid, chloric acid and tungstic acid. Also, in the process of the present invention, the oxidation catalyst may be employed together with a complexing agent for metal ions, selected from, for example, phosphoric acid complexing agents such as phosphoric acid, alkyl phosphates and polyphosphoric acid.

In the process of the present invention, the oxidation catalyst is preferably employed in a total amount of 1 to 1000 ppm, more preferably 30 to 200 ppm, based on the amount in weight of the monohydric phenolic compound fed into the first reactor.

The process of the present invention can be carried out by using the continuous multi-stage oxidation apparatus as shown in FIG. 2, which has four reactors 1, 10, 20 and 30 connected to each other in series, and in which a monohydric phenolic compound is catalytically oxidized, at a low conversion thereof, to produce dihydric phenolic compounds with a high selectivity thereof.

Referring to FIG. 2, a monohydric phenolic compound is fed at a temperature of 30 to 100° C., preferably 40 to 95° C. into a lower portion of the first reactor 1 through a feed line 2, and a portion of a peroxide compound (particularly hydrogen peroxide), a portion of a catalyst and optionally a ketone compound are fed into the lower portion of the first reactor 1 respectively through feed lines 3, 4 and 5. In the first reactor, the monohydric phenolic compound is catalytically oxidized with the peroxide compound to produce corresponding dihydric phenolic compounds, while flowing upward from the lower portion to the top portion through the middle portion of the first reactor 1. The reaction mixture produced in the first reactor 1 is delivered from the top portion of the first reactor 1 through a delivery line 7, is cooled by a cooler (heat-exchanging cooler) 6 to a temperature of 40 to 100° C. The cooled reaction mixture is fed into the lower portion of the second reactor 10 through a feed line 12, and a portion of the peroxide compound and optionally a portion of the catalyst are fed into the lower portion of the second reactor 10 through the feed lines 13 and 14, respectively. The reaction mixture is subjected to a catalytic oxidation reaction of the monohydric phenolic compound with the peroxide compound while passing upward through the reactor 10. The reaction mixture produced in the second reactor 10 is delivered from a top portion of the second reactor 10 through a delivery line 17 and is directly fed into a lower portion of a third reactor 20 through a feed line 22 connected to the delivery line 17. A reaction mixture produced in the third reactor 20 is delivered from a top portion of the third reactor 20 through a delivery line 27, is cooled by a cooler 26 to a temperature of 40 to 100° C., and then is fed into a lower portion of a fourth reactor 30 through a feed line 32. Also, a remaining portion of the peroxide compound is fed into the lower portion of the fourth reactor 30 through a feed conduit 33. Optionally a supplementary amount of the catalyst is fed into the lower portion of the fourth reactor 30 through a feed line 34. A reaction mixture produced in the fourth reactor 30 is delivered from a top portion of the fourth reactor 30 through a delivery line 37 and is heat-exchanged by a heat exchanger 35. The resultant reaction mixture having a desired temperature and containing the target dihydric phenolic compounds is withdrawn from the heat-exchanger through a withdrawal line 38.

In the process of the present invention as shown in FIG. 2, a monohydric phenol compound for example, phenol is oxidized to produce dihydric phenolic compounds, for example, catechol and hydroquinone at a high selectivity thereof.

In the process of the present invention using the continuous four stage oxidation apparatus as shown in FIG. 2, the reaction mixture delivered from the first reactor is preferably cooled by the cooler 6 to a temperature of 40 to 100° C., more preferably 50 to 95° C., and the temperature of the reaction mixture passing through each reactor is preferably controlled to 40 to 120° C., more preferably 55 to 115° C., to catalytically oxidize the mono-hydric phenolic compound under moderate conditions.

In the process of the present invention, as shown in FIGS. 1 and 2, the catalyst can be fed into the continuous multi-step oxidation apparatus in such a manner that a portion of the total amount of the catalyst is fed into the first reactor, and the remaining portion of the catalyst is dividedly fed into one or more of the succeeding reactors, for example, the second and third reactors 10 and 20 of FIG. 1 or the second and fourth reactors 10 and 30 of FIG. 2.

When the oxidation apparatus of FIG. 2 is employed, the reaction mixture delivered from the second reactor 10 through the delivery line 17 has a relatively low temperature of about 80 to 110° C., and thus is fed into the third reactor 20 without feeding additional amounts of the peroxide compound and the catalyst. Therefore, the non-reacted monohydric phenolic compound, peroxide compound and optionally ketone compound contained in the reaction mixture fed from the second reactor 10 into the third reactor 20 are subjected to the oxidation reaction of a temperature of 120° C. or less in the third reactor 20. Namely, the oxidation reaction of the monohydric phenolic compound is continuously carried out in the second and third reactors 10 and 20.

In the process of the present invention, each of the catalyst and the ketone compound can be fed in an entire amount thereof into the first reactor, without feeding into the succeeding reactors. Alternatively, each of the catalyst of the ketone compound may be dividedly fed in one or more of the succeeding reactors, as long as the amount of the catalyst or the ketone fed into each proceeding reactor is similar to that of the peroxide compound fed into the proceeding reactor.

In the process of the present invention, when the reaction mixture delivered from the rearend reactor (the third reactor 20 of FIG. 1 or the fourth reactor 30 of FIG. 2) through the delivery line 27 in FIG. 1 or the delivery line 37 in FIG. 2 contains non-reacted monohydric phenolic compound and peroxide compound, the temperature of the delivered reaction mixture is adjusted, for example, is heated or cooled to a desired level, for example, about 80 to 125° C., by a heat-exchanger 25 in FIG. 1 or a heat-exchanger 35 in FIG. 2, and the temperature-adjusted reaction mixture is preferably transported to and stored in a storage container (not shown in FIGS. 1 and 2) wherein the non-reacted monohydric phenolic compound is oxidized with the non-reacted peroxide compound, as an aging reaction, to completely consume the peroxide compound.

As mentioned above, the reaction mixture withdrawn from the rearend reactor of the continuous multi-stage oxidation apparatus is optionally subjected to the aging reaction. The aged or non aged reaction mixture contains the target dihydric phenolic compounds, for example, catechol and hydroquinone, together with the non-reacted monohydric phenolic compound, the catalyst and optionally the non-reacted ketone compound. The reaction mixture is subjected to a refining procedure, for example, a distillation refining procedure, to separate the compounds from each other, to collect the target dihydric phenolic compounds and to separately recover the catalyst and the non-reacted ketone compound and monohydric phenolic compound.

The continuous multi-stage oxidation apparatus of the present invention for producing a dihydric phenolic compound comprises a plurality of oxidation reactors connected to each other in series. In FIG. 1, the oxidation apparatus comprises a first reactor 1 and two reactors 10 and 20 succeeding to the first reactor 1. The first reactor 1 is connected to a feed source (not shown) of a monohydric phenolic compound through a feed line 2, to a feed source (not shown) of a peroxide compound through a feed line 3, to a feed source (not shown) of a catalyst through a feed line 4 and optionally to a feed source (not shown) of a ketone compound through a feed line 5. At least one of the succeeding reactors 10 and 20 is connected to a feed source (not shown) of the peroxide compound through a feed line 13 or 23 and optionally to a feed source (not shown) of the catalyst through a feed line 14 or 24. The rearend reactor (the third reactor) 20 has an outlet for delivery a final reaction mixture produced therein.

The oxidation apparatus of the present invention optionally comprises at least one cooling means 6 or 16 each arranged between the succeeding reactor 10 or 20 connected to the peroxide compound-feed source through a feed line 13 or 23 and a next succeeding reactor 1 or 10 located in front of the succeeding reactor 10 or 20 connected to the peroxide compound-feed source through the feed line 13 or 23.

In the oxidation apparatus as shown in FIG. 2 in accordance with the present invention, four oxidation reactors 1, 10, 20 and 30 in each of which a reaction mixture can be subjected to the catalytical oxidation reaction while passing therethrough, are connected to each other in series. In the first reactor 1, a feed line 2 for a monohydric phenolic compound, a feed line 3 for a peroxide compound, a feed line 4 for a catalyst and optionally a feed line 5 for a ketone compound are connected to a lower portion of the first reactor 1. Also, the second and fourth reactors 10 and 30 succeeding to the first reactor 1 have feed lines 12 and 32 for the reaction mixtures each produced in a reactor located in front of the second or fourth reactors 10 and 30, feed lines 13 and 33 for the peroxide compound and optionally feed lines 14 and 34 for the catalyst.

Further, a cooling means (cooler) 6 is arranged between the first reactor 1 and the second reactor 10 to cool the reaction mixture delivered from the first reactor 1, and a cooling means (cooler) 26 is arranged between the third reactor 20 and the fourth reactor 30 to cool the reaction mixture delivered from the third reactor 20. The third reactor 20 does not have the feed line for the peroxide compound and the feed line for the catalyst. In the oxidation apparatus of the present invention, the rearend reactor (for example, the third reactor 20 in FIG. 1 and the fourth reactor 30 in FIG. 2) has a heat-exchanger (25 in FIG. 1 and 35 in FIG. 2) by which the temperature of the reaction mixture delivered from the rearend reactor is adjusted to a desired temperature. The temperature-adjusted reaction mixture is transported to and stored in a storage container (tank) (not shown) through a withdrawal line (28 in FIG. 1 and 38 in FIG. 2). In the storage container, the peroxide compound remaining in the withdrawn reaction mixture may consumed by an oxidation reaction of the non-reacted monohydric phenolic compound with the remaining peroxide compound to produce dihydric phenolic compounds.

On the oxidation apparatus of the present invention, there is no limitation to the type of the cooling means for cooling the reaction mixture delivered from a preceding reactor, as long as the reaction mixture in the state of a liquid can be cooled to a desired temperature at which a rapid oxidation of the monohydric phenolic compound with the peroxide compound can be controlled when an additional amount of the peroxide compound is added to the reaction mixture in a succeeding reactor. Preferably, a heat-exchanging cooler using a cooling medium consisting of cold water is used as a cooling means. In the oxidation apparatus of the present invention, the succeeding reactors connected to a feed line for the peroxide compound is preferably further connected to a feed line for the catalyst.

In the oxidation apparatus of the present invention, each reactor is preferably of a cylindrical type such that no backward flow of the reaction mixture occurs in the reactor. If necessary, as shown in FIGS. 1 and 2, the reactors are provided with partitioning plates 9, 19, 29 and 39, for example, perforated plates or baffles. The type and scale of the reactors may be designed in consideration of the conversion (reaction degree) of the monohydric phenolic compound, the amounts of the peroxide compound, the catalyst and optionally the ketone compound used, and the increase in temperature of the reaction mixture. The reactors may be the same as or different from each other in type and scale (size) thereof.

The reaction mixture withdrawn from the heat exchanger connected to the rearend reactor may be transported to and aged in the storage container, and then the aged reaction mixture may be subjected to a recovery procedure for the non-reacted monohydric phenolic compound. Alternatively, the reaction mixture delivered from the rearend reactor may be directly subjected to the recovery procedure for the non-reacted monohydric phenolic compound.

In the non-reacted monohydric phenolic compound-recovery procedure, the reaction mixture is subjected to a distillation procedure by which the monohydric phenol compound is recovered as a distillation vapor fraction, and a non-vaporized liquid fraction containing the target dihydric phenolic compound in an increased concentration is obtained. The vapor fraction obtained by the distillation is refined to remove water, and to obtain a mixture containing the ketone compound and by-products, for example, aliphatic carboxylate esters. The mixture may be returned to the first reactor and reused for the oxidation reaction.

The monohydric phenolic compound recovered by the above-mentioned distillation procedure is recycled and fed, together with fresh monohydric phenolic compound, into the first reactor, and is reused for the oxidation procedure, at a low conversion, of the monohydric phenolic compound. The recycling amount of the recovered monohydric phenolic compound is preferably 10 to 100 times, more preferably 17 to 33 times, the total amount of the monohydric phenolic compound consumed in the oxidation procedure or the amount of the fresh monohydric phenolic compound fed into the first reactor.

The recovered mixture obtained by the distillation procedure for recovering the non-reacted monohydric phenolic compound and containing the target compounds in a high concentration of 80 to 100% by weight, particularly 85 to 95% by weight, is subjected to further distillation procedures in which the individual compounds in the mixture are successively separated from each other. In this procedures, for example, catechol and hydroquinone are separated from each other and refined.

EXAMPLES

The present invention will be further explained by the following examples.

Example 1

A continuous multi-stage oxidation apparatus as shown in FIG. 2 was used for a continuous multi-stage oxidation procedure for phenol. This multi-stage oxidation procedure was continuously carried out at a low conversion of phenol for 40 days.

In the oxidation apparatus as shown in FIG. 2, the inside volumes of the individual reactors are 1.1 m$^3$ in the first reactor 1, 3.2 m$^3$ in the second reactor 10, 3.2 m$^2$ in the third reactor 20 and 11.3 m$^3$ in the fourth reactor 30. Also, the inner diameter of the individual reactors are 600 mm in the first reactor 1, 650 mm in the second reactor 10, 650 mm in the third reactor 20 and 1200 mm in the fourth reactor 30.

In the first reactor 1, (a) a mixture of a recovered (recycling) phenol containing 0.36% by weight of catechol and having a temperature of about 75° C. at a feed rate of 16,054 kg/hr and fresh phenol having a temperature of about 70° C. at a feed rate of 661 kg/hr; (b) a catalyst comprising sulfuric acid at a feed rate of 0.65 kg/hr and an additive consisting of phosphoric acid at a feed rate of 0.16 kg/hr; (c) an aqueous hydrogen peroxide containing 60% by weight of hydrogen peroxide at a feed rate of 146 kg/hr; and (d) a mixture of a recovered light fraction mixture comprising about 50% by weight of diethylketone and about 50% by weight of ethyl propionate at a feed rate of 654 kg/hr with fresh diethylketone at a feed rate of 18 kg/hr, were fed altogether into a lower portion of the first reactor, to allow the fed reaction mixture to pass upward through the first reactor 1 for a residing time of 3.5 minutes, while catalytically oxidizing phenol with hydrogen peroxide. Then the resultant reaction mixture was delivered at a temperature of 89° C. from the top portion of the first reactor 1, cooled to a temperature of 80° C. by a cooler 6 and then fed into the bottom portion of the second reactor 10.

Into the bottom portion of the second reactor 10, sulfuric acid was fed as a catalyst at a feed rate of 0.65 kg/hr and an aqueous hydrogen peroxide solution containing 60% by weight of hydrogen peroxide was fed at a feed rate of 146 kg/hr, together with the reaction mixture delivered from the first reactor 1. The fed reaction mixture was allowed to pass upward the second reactor 10 for a residing time of 10.0 minutes, to catalytically oxidize phenol with hydrogen oxide. The resultant reaction mixture having an increased temperature of 98° C. was delivered from a top portion of the second reactor 10 and fed into a bottom portion of the third reactor 20. The fed reaction mixture passed upward through the third reactor for a residing time of 10.0 minutes, while oxidizing phenol with hydrogen peroxide. The resultant reaction mixture having an increased temperature of 100° C. was delivered from a top portion of the third reactor 20. The delivered reaction mixture was cooled to a temperature of 89.5° C. by a heat-exchanger type cooler 26. The cooled reaction mixture was fed into a bottom portion of the fourth reactor 30.

In the bottom portion of the fourth reactor 30, a catalyst consisting of sulfuric acid was fed at a feed rate of 0.65 kg/hr and an aqueous hydrogen peroxide solution containing 60% by weight of hydrogen peroxide was fed at a feed rate of 146 kg/hr, together with the reaction mixture delivered from the third reactor 20.

In the fourth reactor 30, the fed reaction mixture passed upward therethrough, for a residing time of 36.0 minutes, while oxidizing phenol with hydrogen peroxide. Then the resultant reaction mixture having an increased temperature of 106.7° C. was delivered from a top portion of the fourth reactor 30 at a delivery rate of 17,827 kg/hr, and was temperature-adjusted to a temperature of 115° C. by a heat exchanger 35.

The temperature-adjusted reaction mixture was aged in a storage tank (not shown in FIG. 2) to completely consume hydrogen peroxide contained in the reaction mixture.

The resultant reaction mixture in the storage tank contained 89.8% by weight of the non-reacted phenol, 3.8% by weight of a mixture of diethylketone with ethyl propionate, 2.7% by weight of catechol, 1.7% by weight of hydroquinone, 1.6% by weight of water and a very small amount of the remaining catalyst.

The reaction mixture was subjected to distillation procedures to recover the phenol. In the first distillation procedure, a light fraction comprising water and diethylketone is removed as a vapor fraction and then, the remaining liquid fraction is subjected to a second distillation procedure to collect the non-reacted phenol as a vapor fraction having a phenol content of 96.3% by weight. The collected phenol-containing vapor fraction is liquefied and recycled to the first reactor 1. Also, a liquid fraction containing 53.5% by weight of catechol, 37.4% by weight of hydroquinone, and 9.1% by weight of the others was recovered at a recovery rate of 783 kg/hr.

The liquid fraction obtained by the non-reacted phenol-recovering distillation procedure is subjected to a third distillation procedure by which catechol having a degree of purity of 99% by weight or more was collected at a collecting rate of 387 kg/hr and hydroquinone was obtained at a collecting rate of 281 kg/hr.

In the above-mentioned oxidation procedures for phenol by using the continuous multi-stage oxidation apparatus, the molar ratio of the amount of phenol fed into the first reactor 1 to the total amount of hydrogen peroxide fed into the oxidation apparatus was 23, and in each of the first, second and fourth reactors, the molar ratio of the amount of phenol fed into the first reactor 1 to the amount of hydrogen peroxide fed into each reactor was 69. Also, it was confirmed that the temperature of the reaction mixture passing through the oxidation apparatus including the four reactors did not exceed 110° C.

In the above-described example, the conversion of phenol (which refers to molar % of the amount of phenol consumed in the oxidation apparatus to the amount of phenol fed into the first reactor) was about 3.9%, the selectivity of catechol was 55.9 molar %, the selectivity of hydroquinone was 40.0 molar %. Also, in this example, the conversion of hydrogen peroxide was substantially 100%. Further, the selectivity of catechol and hydroquinone was 85.4% based on the molar amount of hydrogen peroxide.

Comparative Example 1

The same oxidation procedures for phenol with hydrogen peroxide as in Example 1 were carried out except that a single reactor was employed. Namely, phenol in the same amount as used in Example 1, hydrogen peroxide in the same amount as the total amount used in Example 1, the catalyst in the same amount as the total amount used in Example 1 and the ketone compound in the same amount as in Example 1 were fed into the single reactor, and the oxidation procedure was carried out until the conversion of phenol reached about 3.9 molar %. In the single reactor, a heat of reaction was generated and thus the temperature of the reaction mixture increased by about 52° C.

Namely, when phenol was oxidized by feeding phenol, hydrogen peroxide, sulfuric acid and diethylketone at a temperature of 75° C. into the single reaction, the temperature of the reaction mixture rose to 127° C. which is higher than a threshold temperature of explosion of diethylketone peroxide, namely, 120 to 125° C., and thus the resultant reaction system was very dangerous in industrial practice. In the oxidation procedure at the above-mentioned high temperature, the total yield of catechol and hydroquinone based on hydrogen peroxide was 75%, and the resultant reaction mixture was significantly colored and contained many by-products. Also, the selectivity of catechol and hydroquinone was low.

The process and apparatus of the present invention are useful for producing dihydric phenolic compounds by continuously catalytically oxidizing a monohydric phenolic compound in industrial practice with a high selectivity of the dihydric phenolic compounds. Also, in the process of the present invention, the explosion of ketone peroxide produced during the oxidation procedure can be surely prevented.

What is claimed is:

1. A process for producing a dihydric phenolic compound comprising oxidizing a monohydric phenolic compound in the presence of a catalyst by using a continuous multi-stage oxidation apparatus, comprising a plurality of oxidation reactors connected to each other in series, in such a manner that (1) in a first reactor of the oxidation apparatus, a monohydric phenolic compound having a temperature of 30 to 100° C., a peroxide compound and a catalyst are fed thereinto, to oxidize the monohydric phenolic compound into a dihydric phenolic compounds, and the resultant reaction mixture containing the produced dihydric phenolic compound, the non-reacted monohydric compound, the non-reacted peroxide compound and the catalyst is delivered from the first reactor; (2) the reaction mixture delivered from the first reactor is passed through one or more reactors succeeding to the first reactor, to further oxidize the non-reacted monohydric phenolic compound, while, in the steps (1) and (2), a portion of the peroxide compound is fed into the first reactor and the remaining portion of the peroxide compound is fed into at least one succeeding reactor; and (3) a final reaction mixture produced in a rearend reactor and comprising the produced dihydric phenolic compound, the non-reacted monohydric phenolic compound, the non-reacted peroxide compound and the catalyst is delivered from the oxidation apparatus.

2. The dihydric phenolic compound-producing process as claimed in claim 1, wherein at least one ketone compound is fed together with the monohydric phenolic compound, the peroxide compound and the catalyst into the first reactor.

3. The dihydric phenolic compound-producing process as claimed in claim 1, wherein before the remaining portion of the peroxide compound is fed into at least one reactor succeeding to the first reactor, the reaction mixture delivered from a next reactor located in front of the succeeding reactor to which the remaining portion of the peroxide compound is fed is cooled to a temperature of 40 to 100° C. by a cooling means, and then is fed, together with the remaining portion of the peroxide compound, into the succeeding reactor, and the temperature of the reaction mixture passing through the oxidation apparatus is controlled to a level of 40 to 120° C.

4. The dihydric phenolic compound-producing process as claimed in claim 1, wherein the continuous multi-stage oxidation apparatus comprises 2 to 10 oxidation reactors connected to each other in series.

5. The dihydric phenolic compound-producing process as claimed in claim 1, wherein the amount of the monohydric phenolic compound and the total amount of the peroxide compound fed into the continuous multi-stage oxidation apparatus are controlled to a molar ratio of 10:1 to 100:1.

6. The dihydric phenolic compound-producing process as claimed in claim 1, wherein the amount of the monohydric phenolic compound fed into the first reactor and the amount of the peroxide compound fed into each of the first reactor and the at least one succeeding reactor are controlled to a molar ratio of 33:1 to 1000:1.

7. The dihydric phenolic compound-producing process as claimed in claim 1, wherein the monohydric phenolic compound is selected from the group consisting of phenolic monoalkyl phenols of which the alkyl group has 1 to 6 carbon atoms.

8. The dihydric phenolic compound-producing process as claimed in claim 1, wherein the peroxide compound is selected from the group consisting of hydrogen peroxide, perchloric acid, ketone peroxides and aliphatic percarboxylic acids.

9. The dihydric phenolic compound-producing process as claimed in claim 2, wherein the ketone compound is selected from dialkylketones of which each alkyl group has 1 to 9 carbon atoms.

10. The dihydric phenolic compound-producing process as claimed in claim 2, wherein the ketone compound is fed in an amount of 0.5 to 10% by weight based on the amount of the monohydric phenolic compound fed into the first reactor.

11. The dihydric phenolic compound-producing process as claimed in claim 2, wherein the ketone compound is fed in an amount of 0.1 to 10 moles per mole of the peroxide compound fed into the oxidation apparatus.

12. The dihydric compound-producing process as claimed in claim 1, wherein the catalyst comprises at least one member selected from the group consisting of phosphoric acid, sulfuric acid, chloric acid and tungstic acid.

13. The dihydric phenolic compound-producing process as claimed in claim 1, wherein the catalyst is fed in an amount of 1 to 1000 ppm based on the amount of the monohydric phenolic compound fed into the first reactor.

* * * * *